United States Patent
Jorquera Nieto et al.

(10) Patent No.: US 7,332,577 B2
(45) Date of Patent: Feb. 19, 2008

(54) THERAPEUTIC HUMAN ALBUMIN SOLUTIONS WITH LOW PREKALLIKREIN ACTIVATOR (PKA) ACTIVITY AND PROCESS FOR OBTAINING THEM

(75) Inventors: Juan Ignacio Jorquera Nieto, Ametlla del Valles (ES); Olga Santaeularia Lozano, Barcelona (ES); Nuria Hosta Mateu, Barcelona (ES)

(73) Assignee: Grifols, S.A., Barcelona (ES)

( * ) Notice: Subject to any disclaimer, the term of this patent is extended or adjusted under 35 U.S.C. 154(b) by 0 days.

(21) Appl. No.: 11/185,613

(22) Filed: Jul. 19, 2005

(65) Prior Publication Data

US 2006/0020117 A1    Jan. 26, 2006

(30) Foreign Application Priority Data

Jul. 26, 2004   (ES)   ................. 200401830

(51) Int. Cl.
C07K 14/00  (2006.01)
C07K 16/00  (2006.01)
A61K 35/14  (2006.01)

(52) U.S. Cl. ............... 530/362; 530/363; 530/364; 530/380; 530/381; 530/393

(58) Field of Classification Search ............... 530/362, 530/363, 364, 380, 381, 393
See application file for complete search history.

(56) References Cited

U.S. PATENT DOCUMENTS

| | | | |
|---|---|---|---|
| 4,251,510 A | | 2/1981 | Tankersley |
| 4,378,346 A | | 3/1983 | Tankersley |
| 4,900,720 A | * | 2/1990 | Kotitschke ............... 514/21 |
| 5,094,949 A | | 3/1992 | Linnau |
| 5,407,671 A | | 4/1995 | Behringwerke et al. |

FOREIGN PATENT DOCUMENTS

| | | |
|---|---|---|
| EP | 0246439 | 11/1987 |
| EP | 0253198 | 1/1998 |
| EP | 1413312 | 4/2004 |
| WO | WO-97/31947 | 9/1997 |
| WO | WO-00/56768 | 9/2000 |
| WO | WO-2004/047859 A2 | 6/2004 |

OTHER PUBLICATIONS

QIAexpressionist, Fifth Edition, Qiagen, Mar. 2001, pp. 18-20.*
Medline Plus, Medical Encyclopedia: Antithrombin III, A.D.A.M. Inc., 2005, pp. 1-3.*
Yap, H.B. et al.; "Development of a process for the preparation of human serum albumin using chromatographic methods"; Biotechnology of Blood Proteins, 1993, vol. 227, pp. 143-149; ISSN: 0768:3154.
Tanaka, K., et al., "Purification of human albumin by the combination of the method of Cohn with liquid chromatography"; Brazilian Journal of Medical and Biological Research, Nov. 1998, vol. 31, pp. 1383-1388; ISSN: 0100-879X.
Matejtschuk, P. et al. 2000. Production of human albumin solution: a continually developing colloid. British Journal of Anaesthesia 85(6) 887-895.
Human Albumin Solution. Jan. 2006:0255. European Pharmacopoela 5.3: 3511-3513.

* cited by examiner

*Primary Examiner*—Jon Weber
*Assistant Examiner*—Rita Mitra
(74) *Attorney, Agent, or Firm*—Darby & Darby, P.C.

(57) ABSTRACT

The invention discloses a purified albumin solution of human origin with low prekallicrein activator (PKA) activity and stability over time characterised in that it has an antithrombin content equal to or greater than 0.03 mg/g of albumin, and a process for production thereof by the partial extraction of the antithrombin during fractionation of the human plasma.

2 Claims, No Drawings

THERAPEUTIC HUMAN ALBUMIN SOLUTIONS WITH LOW PREKALLIKREIN ACTIVATOR (PKA) ACTIVITY AND PROCESS FOR OBTAINING THEM

The present invention relates generally to therapeutic human albumin solutions with low prekallicrein activator (PKA) activity, which are stable over time, and also to a process for reducing prekallicrein activator activity in purified albumin solutions of human origin.

STATE OF THE ART

Coagulation factor XII (Hageman factor) is a protein having a molecular weight of approximately 80,000 which, in its activated form, consists of fragments thereof having a molecular weight of approximately 28,000. This activated factor XII (fXIIa) acts as a prekallicrein activator (PKA).

Apart from its action on blood coagulation mechanisms, PKA acts on prekallicrein, catalysing its conversion to kallicrein which adversely affects the conversion from kininogen to bradykinin. Bradykinin is a potent vasodilator which can cause incidences of hypotension. The kallicrein formed also catalyses the formation of PKA, feeding back the process.

Purified human plasma albumin solutions are therapeutically useful and are widely used to increase blood volume in cardiovascular surgery, among other uses.

However, the hypotensive effect caused by the rapid infusion of human albumin solutions is one of the adverse reactions, which is serious in specific cases and frequently occurs in conjunction with this infusion of albumin.

PKA may be present as a contaminant in these human albumin solutions, as it is generated from factor XII by contact with foreign surfaces during the albumin purification process and for other reasons, so its content in said solutions has been limited to levels of less than 35 IU/ml (European Pharmacopoeia).

In batches of commercial albumin, which have low PKA levels on the production date, it has been found that the PKA level increases over time during the storage thereof within the established period of stability.

Starting from this state of the art, the inventors proposed to find therapeutic human albumin solutions having low prekallicrein activator (PKA) activity and also ensuring significant stability of the PKA levels in the commercial albumin solution for the established storage period so that a therapeutic human albumin solution with a very low level of prekallicrein activator is clinically available at any time within a previously established long storage period.

After carrying out extensive research and investigations, the inventors have found that it is possible to anticipate the generation of PKA activity in a human albumin solution and simultaneously to obtain a high degree of stability over time by setting limits to the quantity of antithrombin in the final albumin and, specifically, with an antithrombin content greater than or equal to 0.03 mg/g of albumin, giving rise to the present invention.

The albumin solution according to the present invention is obtained by partial extraction of the antithrombin in a phase of fractionation of human plasma, and, in particular, by chromatographic extraction, for example, from the plasma, the cryoprecipitation supernatant, the fraction I supernatant or the II+III supernatant.

This partial extraction of the antithrombin may be carried out by influencing the parameters that control the chromatographic stage, for example by varying the chromatography load relationship, so that the effluent contains sufficient antithrombin to detect a concentration greater than or equal to 0.03 mg of active antithrombin/g of albumin in the final albumin.

In a preferred embodiment, only a portion of the total volume that will yield the final batch of albumin is subjected to chromatographic extraction, the materials that have been subjected to extraction subsequently being mixed with those that have not been extracted. This may be achieved by mixing plasmas, supernatants (of cryoprecipitate, FrI or FrII+III) or fractions (FrIV or FrV) from which the antithrombin has been extracted with others that have not been subjected to said extraction. This mixture should be in a proportion that is sufficient to detect an antithrombin concentration greater than or equal to 0.03 mg of antithrombin/g of albumin in the final albumin.

A practical example of an albumin solution according to the invention is given hereinafter merely as an example.

EXAMPLE 1 albumin was prepared from FrV, and the antithrombin was extracted from the FrII+III supernatant by heparin-agarose affinity chromatography.

Table 1 shows the antithrombin content of the albumin (final product in concentration of 20%) as a function of the percentage (%) of the volume of FrII+III supernatant from which the antithrombin has been extracted by chromatography.

TABLE 1

| Extraction of antithrombin in supernatant fractions FII + FIII % | Antithrombin content (mg/ml) in final product (20% alb.) | Antithrombin content (mg/g of albumin) in final product |
|---|---|---|
| 0 (n = 5) | 0.020 | 0.1 |
| 50 (n = 2) | 0.013 | 0.065 |
| 80 (n = 5) | 0.0078 | 0.039 |
| 100 (n = 6) | <0.006 | <0.03 |

The antithrombin was extracted in supernatant fractions of 0, 50, 80 and 100% respectively while mixing with the corresponding portions of FII+FIII without antithrombin extraction.

It has been found that, when extracting 100% of antithrombin from the FII+III supernatant, no antithrombin (value lower than the limit of detection of the method) was detected in the albumin (final product). It has also been found that, when extracting 80% of antithrombin from the FrII+III supernatant and mixing with the remaining 20% (from which the antithrombin has not been extracted), 0.0078 mg of antithrombin per ml of 20% albumin solution are detected.

Table 2 shows the development over time at 5° C. of PKA activity (IU) in 20% albumin solutions (final product) in relation to the percentage of extraction of antithrombin achieved in the FrII+III supernatant.

TABLE 2

| process | Extraction of antithrombin (%) | 0 | 1 | 2 | 3 | 5 | 6 | 8 | 9 | 12 |
|---|---|---|---|---|---|---|---|---|---|---|
| 1 | 0 | <2.0 | <2.0 | <2.0 | — | 2.4 | — | <2.0 | — | <2.0 |
| 2 | 0 | <2.0 | <2.0 | <2.0 | — | <2.0 | — | <2.0 | — | <2.0 |
| 3 | 50 | <2.0 | <2.0 | <2.0 | — | <2.0 | — | <2.0 | — | <2.0 |
| 4 | 50 | <2.0 | <2.0 | <2.0 | — | <2.0 | — | <2.0 | — | 2.5 |
| 5 | 80 | <2.0 | <2.0 | — | 2.9 | 3.0 | — | — | 3.2 | 5.7 |
| 6 | 80 | 2.2 | 3.0 | 3.5 | 4.4 | — | 2.3 | — | 6.0 | 5.6 |
| 7 | 100 | 8.9 | 18.5 | — | 18.2 | 15.4 | — | — | 22.3 | 24.2 |
| 8 | 100 | 10.6 | 23.3 | — | 24.9 | 24.0 | — | — | 32.1 | 32.8 |

It has been found that in the processes in which 100% of antithrombin was extracted from the FII+III supernatant, the PKA activity level is higher from the beginning in the albumin (final product) and, increases so as to approach the limit set by the European Pharmacopoeia over twelve months. Conversely, in the processes involving controlled or partial extraction of the antithrombin, the PKA activity level in the albumin solution remains at low or undetectable levels.

The description serves merely as an example and does not limit the scope of the invention, which will merely be defined by the appended claims, with due consideration of equivalents and variations that may be implemented by experts in the art with knowledge of the present invention and that are also included within the scope thereof.

The invention claimed is:

1. A purified human albumin solution for therapeutic use comprising albumin and having an active antithrombin content ranging from 0.03 to 0.10 mg/g of albumin, and a prekallikrein (PKA) activity that remains below 35 IU/ml over time.

2. The purified human albumin solution of claim 1, wherein PKA activity remains below 35 IU/ml for at least twelve months.

* * * * *